US009440915B2

(12) United States Patent  
Yi

(10) Patent No.: US 9,440,915 B2  
(45) Date of Patent: Sep. 13, 2016

(54) METHOD FOR PREPARING METHANEDISULFONIC ACID

(71) Applicant: Hunan Astar Bio-chemical Technology Co., Ltd., Jinshi, Hunan (CN)

(72) Inventor: Zongming Yi, Jinshi (CN)

(73) Assignee: HUNAN ASTAR BIO-CHEMICAL TECHNOLOGY CO., LTD., Jinshi, Hunan (CN)

(*) Notice: Subject to any disclaimer, the term of this patent is extended or adjusted under 35 U.S.C. 154(b) by 0 days.

(21) Appl. No.: 14/647,607

(22) PCT Filed: Sep. 28, 2012

(86) PCT No.: PCT/CN2012/082330  
§ 371 (c)(1),  
(2) Date: May 27, 2015

(87) PCT Pub. No.: WO2014/047883  
PCT Pub. Date: Apr. 3, 2014

(65) Prior Publication Data  
US 2015/0353484 A1   Dec. 10, 2015

(51) Int. Cl.  
*C07C 303/02* (2006.01)

(52) U.S. Cl.  
CPC .................. *C07C 303/02* (2013.01)

(58) Field of Classification Search  
CPC ................................................ C07C 303/02  
See application file for complete search history.

(56) References Cited

U.S. PATENT DOCUMENTS

| 2,492,938 A | 12/1949 | Rosher |
| 2,493,038 A | 1/1950 | Snyder |
| 2,842,589 A | 7/1958 | Crowder |
| 2006/0155142 A1 | 7/2006 | Werner |

FOREIGN PATENT DOCUMENTS

| CN | 1129213 A | 8/1996 |
| CN | 102887840 A | 1/2013 |

OTHER PUBLICATIONS

International Search Report in international application No. PCT/CN2012/082330, mailed on Jul. 4, 2013.  
English Translation of the Written Opinion of the International Search Authority in international application No. PCT/CN2012/082330, mailed on Jul. 4, 2013.

*Primary Examiner* — Shailendra Kumar  
(74) *Attorney, Agent, or Firm* — Oppedahl Patent Law Firm LLC

(57) ABSTRACT

Disclosed is a method for preparing methanedisulfonic acid, comprising an acidification, wherein the acidification comprises that methanedisulfonate reacts with an acidifier to form a mixture containing methanedisulfonic acid. The disclosure has high yield, low cost, and the process are environmental friendly.

19 Claims, No Drawings

METHOD FOR PREPARING METHANEDISULFONIC ACID

This application is a 371 of PCT/CN2012/082330, filed on Sep. 28, 2012.

TECHNICAL FIELD

This disclosure relates to the field of organic chemistry, in particular to a method for preparing methanedisulfonic acid.

BACKGROUND

Methanedisulfonic acid is also known as methionic acid, methylenedisulfonic acid, methyl disulfonic acid or methane-disulfonic acid and has English names of Methanedisulfonic acid (MDSA), Methionic acid or Methanedisulphonic acid, of which the CB Number is CB 9742754, molecular formula is $CH_4O_6S_2$, the molecular weight is 176.17, CAS is 503-40-2, and the structural formula is:

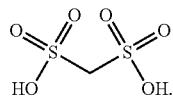

Methanedisulfonic acid is an alkyl disulfonic acid with the shortest carbon chain, has a variety of special physical and chemical properties, and is widely used in electronics, surface treatment, medicine, battery and other industries.

U.S. Pat. No. 2,492,938, U.S. Pat. No. 2,493,038 reported a method for preparing the compound by the reaction of "methane with sulfur trioxide". The reaction process is shown as follows:

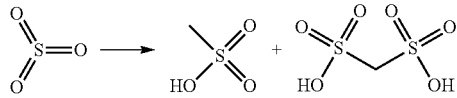

However, the method finally obtains a mixture of several acids such as methanedisulfonic acid, methanesulfonic acid, sulfuric acid and so on, which is quite difficult to be separated. Thus, it is very difficult to obtain methanedisulfonic acid that meets the quality requirements.

U.S. Pat. No. 2,842,589 disclosed a preparation of methanedisulfonic acid by the reaction of "methanesulfonic acid with sulfur trioxide":

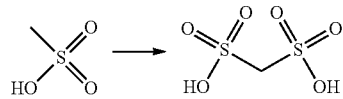

The method is similar as the method utilizing the reaction of "methane with sulfur trioxide", and also has a problem of purification.

Sartori, Pete et al. (Sartori, Peter; Jueschke, Ralf; Boese, Roland; Blaeser, Dieter; Zeitschrift fuer Naturforschung, B; Chemical Sciences; vol. 49; nb. 11 (1994); p. 1467-1472) reported a method for preparing methanedisulfonic acid by the hydrolysis of "methanedisulfonyl chloride", and the reaction formula is shown as follows:

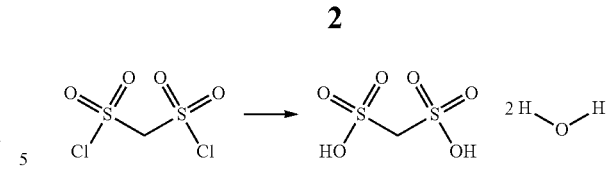

However, the preparation of dimethylsulfamoyl chloride is more difficult than that of methanedisulfonic acid, and thus this method cannot be industrialized.

Goldwhite, H. et al. (Tetrahedron; vol. 21; 1965; p. 2743-2747) reported a method for preparing methanedisulfonic acid from sodium methanedisulfonate as the raw material by a two-step reaction, the overall reaction of which is shown as follows:

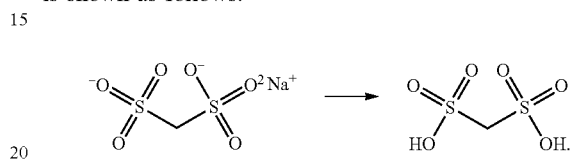

The method additionally has a reaction for preparing sodium methanedisulfonate itself, and thus is actually a three-step reaction. The method has relatively more steps, the purification process is complex, the total yield is low, and there is heavy metal pollution in the procedure. Therefore, it is not conducive to industrial production. The method disclosed in US Patent Application US 2006155142 is similar as the above method. Likewise, CN Patent ZL 95101622.9 disclosed a method for preparing "sodium methanedisulfonate".

In the method for preparing methanedisulfonic acid, it was proposed that "it may be converted by its sodium or potassium salt", but no specific method is known. The inventor tried to prepare methanedisulfonic acid from its sodium or potassium salt by a method of ion exchange, and found that only a mixture of methanedisulfonic acid and the salt thereof was obtained, and the mixture is difficult to be further separated. Moreover, the concentration of the mixture was very low, such that it required a large quantity of energy for a suitable concentration. Therefore, it still requires further research and exploration on how to easily produce high-quality methanedisulfonic acid with a low-cost, high-yield and environmental friendly manner.

SUMMARY

In view of the above, in order to overcome the defects of the prior art, the present disclosure provides a method for preparing methanedisulfonic acid, which has high yield, low cost, and green processes.

In order to achieve the above object, the present disclosure is implemented as follows:

The present disclosure provides a method for preparing methanedisulfonic acid, including a step of an acidification. The acidification includes subjecting a methanedisulfonate to reacting with an acidifier to form a mixture containing methanedisulfonic acid.

Before the acidification the method may further includes a step of a sulphination. The sulphination may include subjecting a sulphinating reagent to reacting with a dihalomethane to form a mixture containing methanedisulfonate.

The method may further include a step of purification after the acidification. The purification may include steps of filtering the mixture containing methanedisulfonic acid obtained after the acidification, concentrating the filtrate obtained after the filtration, decolorizing the obtained concentrated solution with activated carbon, subjecting the concentrated filtrate to a freezing crystallization after removing the activated carbon by filtration, and removing the crystallized substances by filtration, thus obtaining an aqueous solution of methanedisulfonic acid.

The methanedisulfonate may be one or a mixture of two or more selected from a group consisting of calcium methanedisulfonate, barium methanedisulfonate, ferrous methanedisulfonate, ferric methanedisulfonate, silver methanedisulfonate, lead methanedisulfonate. Preferably, it may be calcium methanedisulfonate or barium methanedisulfonate, and calcium methanedisulfonate may be more preferred.

The acidifier may be one or a mixture of two or more selected from a group consisting of sulfuric acid, phosphoric acid, methane sulfonic acid and hydrochloric acid. Preferably, it may be sulfuric acid or phosphoric acid, and sulfuric acid may be more preferred.

The acidification may be performed in water or a polar organic solvent, or a mixture thereof, preferably in water.

A molar ratio of the methanedisulfonate to the acidifier may be 1:0.5-4.0, preferably 1:0.8-1.0, and more preferably 1:0.95.

A reaction temperature of the acidification may be 0-200° C., preferably 80-100° C., and more preferably 95-100° C.

A reaction time of the acidification may be 1-24 hours, preferably 2-6 hours, and more preferably 4 hours.

The sulphinating reagent may be one or a mixture of two or more selected from a group consisting of calcium thiosulfate, barium thiosulfate, ferrous thiosulfate, calcium bisulfite, barium bisulfite, ferrous bisulfite, calcium sulfite, barium sulfite and ferrous sulfite, preferably one or a mixture of two or more selected from a group consisting of calcium thiosulfate, barium thiosulfate, calcium sulfite and barium sulfite. Calcium sulfite may be more preferred.

The dihalomethane may be dichloromethane or dibromomethane, or a mixture thereof, and dichloromethane may be preferred.

The catalyst of the sulphination may be one or a mixture of two or more selected from a group consisting of sodium dodecyl sulfate, cetyl trimethyl ammonium bromide, dodecyl trimethyl ammonium bromide, polyoxyethylene nonyl phenyl ether, polyethylene glycol-400, polyethylene glycol-600, polyethylene glycol-800, tetraethylammonium chloride, tetraethylammonium bromide, tetrabutylammonium chloride and tetrabutylammonium bromide. Polyethylene glycol-400 may be preferred. A molar ratio of the catalyst to the dihalomethane is 1:1-2000.

The sulphination may be performed in water or a polar organic solvent, or a mixture thereof, preferably in water.

The polar organic solvent may be one or a mixture of two or more selected from a group consisting of dimethylsulfoxide, hexamethylphosphoric triamide, N,N-dimethylformamide, N,N-dimethylacetamide, acetonitrile, methanol and ethanol.

A molar ratio of the sulphinating reagent to the dihalomethane may be 1:0.1-10, preferably 1:0.8-1.2, more preferably 1:0.95.

A reaction temperature of the sulphination may be 40-220° C., preferably 130-200° C., and more preferably 180° C.

A reaction time of the sulphination may be 1-24 hours, preferably 8-12 hours, and more preferably 10 hours.

The method for preparing methanedisulfonic acid according to the present disclosure has the following advantages and characteristics:

(1) The raw materials for the reactions of the present disclosure are cheap and easily to be obtained, and the method has a high-total-yield, thus methanedisulfonic acid can be produced with low cost and has remarkable economic benefits.

(2) The raw materials used in the method of the present disclosure and the intermediate product produced during the process are non-toxic, harmless and non-explosive chemicals, and the by-products can be completely recycled, thus the method is environmental friendly.

Further, the method for preparing methanedisulfonic acid according to the present disclosure also has the following advantages and characteristics:

(3) According to the method of the present disclosure, methanedisulfonic acid can be obtained from a sulphinating reagent and a dihalomethane as raw materials via only two steps of reactions, and the intermediate product can be directly used for the next reaction without a separation, therefore the process is simple, short-route, and readily industrialized.

(4) By means of the purification process of the present disclosure, the quality of the product is significantly improved, and the obtained product is of good quality and high purity.

DETAILED DESCRIPTION

The present disclosure is further illustrated with the following specific examples, which, however, are not limitations to the present disclosure.

Example I

Firstly, a sulphination was performed. To a 500 ml autoclave, were added 300 ml of water, 50 g of calcium sulfite, 0.5 g of polyethylene glycol-400 and 18 g of dichloromethane, stirred, heated up to 180° C., and reacted for 10 hours. After the reaction was completed, the solution was cooled to room temperature, and the blow valve was opened to discharge the unreacted dichloromethane, so as to obtain 360 g of the reaction solution containing calcium methanedisulfonate.

Secondly, an acidification was performed. 20 g of a concentrated sulfuric acid with a mass percentage of 98% was dissolved into 180 g of water to prepare a dilute sulfuric acid solution with a mass percentage of 10%. 360 g of the reaction solution obtained after the sulphination was added into a 1,000 ml four-neck reaction flask with a stirrer and a reflux condenser, heated up to 80±2° C. under stirring, and dropwise added with the prepared dilute sulfuric acid solution within 0.5 hour, then kept warm at 80±2° C. for 2 hours to complete the reaction.

Finally, purification was performed. The product obtained after the acidification was cooled to about 10° C., and then subjected to a pumping filtration by a sand core funnel. The filtrate was collected, and the filter cake was washed with a small amount of deionized water, then the filtrate and the washing liquor were combined. The combined solution was vacuum concentrated by a rotatory evaporator (the vacuum degree was about 25 mmHg, the oil bath had a temperature of 70~100° C.) to distill 200 g of water. The concentrated solution was placed into 100 ml three-neck reaction flask, stirred, heated up to 70° C., and decolored by adding 0.1 g of activated carbon therein and keeping warm for 1 hour. The activated carbon was removed by a pumping filtration with a sand core funnel while the solution was hot. The filtrate was collected and placed into a freezer at −10° C. for 24 hours, thus crystallized substances were precipitated, and removed by pumping filtration with the sand core funnel.

The resulted 65 g of the solution after removing the crystallized substances was the aqueous solution of the target compound methanedisulfonic acid.

After the above reactions were completed, the obtained aqueous solution of methanedisulfonic acid was sampling analyzed, and determined that the concentration of methanedisulfonic acid was 50.8% and the total yield of the reactions was 89%.

Example II

Firstly, a sulphination was performed. To a 500 ml autoclave, were added 300 ml of water, 85 g of barium sulfite, 0.5 g of polyethylene glycol-400 and 18 g of dichloromethane, heated up to 180° C. under stirring, and reacted for 10 hours. After the reaction was completed, the solution was cooled to room temperature, and the blow valve was opened to discharge the unreacted dichloromethane, so as to obtain 398 g of the reaction solution containing barium methanedisulfonate.

Secondly, an acidification was performed. 20 g of a concentrated sulfuric acid with a mass percentage of 98% was dissolved into 80 g of water to prepare a dilute sulfuric acid solution with a mass percentage of 20%. 398 g of the reaction solution obtained after the sulphination was added into a 1,000 ml four-neck reaction flask with a stirrer and a reflux condenser, then added with the prepared dilute sulfuric acid solution and heated up to 100±2° C. under stirring, kept warm for 4 hours to complete the reaction.

Finally, purification was performed. The product after the acidification was cooled to about 30° C., then subjected to filtration. The filtrate was collected and the filter cake was washed with a small amount of deionized water, then the filtrate and the washing liquor were combined to obtain a solution about 300 g. The combined solution was vacuum concentrated by a rotatory evaporator (the vacuum degree was about 25 mmHg, the oil bath had a temperature of 70~100° C.) to distill the water. The concentrated solution was then placed into 100 ml three-neck reaction flask, heated up to 70° C. under stirring, and decolorized by adding 0.1 g of activated carbon therein and keeping warm for 1 hour. The activated carbon was removed by filtration while the solution was hot. The filtrate was placed into a freezer at −10° C. for 24 hours, and thus crystallized substances were precipitated, and removed by filtration. The resulted 80 g of the solution after removing the crystallized substances was the aqueous solution of the target compound methanedisulfonic acid.

After the above reactions were completed, the obtained aqueous solution of methanedisulfonic acid was sampling analyzed, and determined that the concentration of methanedisulfonic acid was 46% and the total yield was 88%.

Example III

Firstly, a sulphination was performed. To a 500 ml autoclave, were added 150 ml of water, 40 g of calcium thiosulfate, a calcium hydroxide slurry formed from 10 g of calcium oxide and 150 g of water, 0.5 g of polyethylene glycol-400 and 13.5 g of dichloromethane, heated up to 180° C. under stirring, and reacted for 10 hours. After the reaction was completed, the solution was cooled to room temperature, and the blow valve was opened to discharge the unreacted dichloromethane, so as to obtain 360 g of the reaction solution containing calcium methanedisulfonate.

Secondly, an acidification was performed. 20 g of a phosphoric acid with a mass percentage of 50% was dissolved into 150 g of water to prepare a phosphoric acid solution. 360 g of the reaction solution obtained after the sulphination was added into a 500 ml four-neck reaction flask with a stirrer and a reflux condenser, heated up to 110±2° C. under stirring, and dropwise added with the prepared phosphoric acid solution within 1 hour, then kept warm at 110±2° C. for 3 hours to complete the reaction.

Finally, purification was performed. The product after the acidification was cooled to about 20° C., then subjected to filtration. The filtrate was collected, and the filter cake was washed with a small amount of deionized water, then the filtrate and the washing liquor were combined. The combined solution was vacuum concentrated by a rotatory evaporator (the vacuum degree was about 25 mmHg, the oil bath had a temperature of 70~100° C.) to distill water. The concentrated solution was placed into 100 ml three-neck reaction flask, heated up to 70° C. under stirring, and decolorized by adding 0.1 g of activated carbon therein and keeping warm for 1 hour. The activated carbon was removed by filtration while the solution was hot. The filtrate was collected and placed into a freezer at −10° C. for 24 hours, thus crystallized substances were precipitated, and removed by filtration. The resulted 60 g of the solution after removing the crystallized substances was the aqueous solution of the target compound methanedisulfonic acid.

After the above reactions were completed, the obtained aqueous solution of methanedisulfonic acid was sampling analyzed, and determined that the concentration of methanedisulfonic acid was 46.2% and the total yield of the reaction was 86%.

Example IV

Firstly, a sulphination was performed. To a 500 ml autoclave, were added 300 ml of water, 110 g of silver sulfite, 0.5 g of polyethylene glycol-400 and 18 g of dichloromethane, heated up to 180° C. under stirring, and reacted for 10 hours. After the reaction was completed, the solution was cooled to room temperature, and the blow valve was opened to discharge the unreacted dichloromethane, so as to obtain 420 g of the reaction solution containing silver methanedisulfonate.

Secondly, an acidification was performed. 48 g of a concentrated hydrochloric acid with a mass percentage of 30% was dissolved into 300 g of water to prepare a dilute hydrochloric acid solution. 420 g of the reaction solution obtained after the sulphination was added into a 1,000 ml four-neck reaction flask with a stirrer and a reflux condenser, heated up to 50±2° C. under stirring, and dropwise added with the prepared dilute hydrochloric acid solution within 0.5 hour, then further kept warm at 50±2° C. for 2 hours to complete the reaction.

Finally, purification was performed. The product after the acidification was cooled to about 10° C., then subjected to filtration. The filtrate was collected, and the filter cake was washed with a small amount of deionized water, then the filtrate and the washing liquor were combined. The combined solution was vacuum concentrated by a rotatory evaporator (the vacuum degree was about 25 mmHg, the oil bath had a temperature of 70~100° C.) to distill 300 g of water. The concentrated solution was placed into 100 ml three-neck reaction flask, heated up to 70° C. under stirring, and decolorized by adding 0.2 g of activated carbon therein and keeping warm for 1 hour. The activated carbon was removed by filtration while the solution was hot. The filtrate was collected and placed into a freezer at −10° C. for 24 hours, thus crystallized substances were precipitated, and removed by filtration. The resulted 65 g of the solution after removing the crystallized substances was the aqueous solution of the target compound methanedisulfonic acid.

After the above reactions were completed, the obtained aqueous solution of methanedisulfonic acid was sampling analyzed, and determined that the concentration of methanedisulfonic acid was 46.6% and the total yield was 84.5%.

Example V

Firstly, a sulphination was performed. To a 500 ml autoclave, were added 300 ml of water, 55 g of ferrous sulfite, 0.5 g of polyethylene glycol-400 and 18 g of dichloromethane, heated up to 180° C. under stirring, and reacted for 10 hours. After the reaction was completed, the solution was cooled to room temperature, and the blow valve was opened to discharge the unreacted dichloromethane, so as to obtain 368 g of the reaction solution containing ferrous methanedisulfonate.

Secondly, an acidification was performed. 26 g of a phosphoric acid with a mass percentage of 50% was dissolved into 100 g of water to prepare a dilute phosphoric acid solution. 368 g of the reaction solution obtained after the sulphination was added into a 1,000 ml four-neck reaction flask with a stirrer and a reflux condenser, heated up to 95±2° C. under stirring, and dropwise added with the prepared dilute phosphoric acid solution within 1 hour, then kept warm at 95±2° C. for 1 hour to complete the reaction.

Finally, purification was performed. The product after the acidification was cooled to about 0° C., then subjected to filtration. The filter cake was washed with a small amount of deionized water, then the filtrate and the washing liquor were collected. The combined solution was vacuum concentrated by a rotatory evaporator (the vacuum degree was about 25 mmHg, the oil bath had a temperature of 70~100° C.) to distill water. The concentrated solution was placed into 100 ml three-neck reaction flask, heated up to 70° C. under stirring, and decolorized by adding 0.1 g of activated carbon therein and keeping warm for 1 hour. The activated carbon was removed by filtration while the solution was hot. The filtrate was collected and placed into a freezer at −10° C. for 24 hours, thus crystallized substances were precipitated, and removed by pumping filtration. The resulted 59 g of the solution after removing the crystallized substances was the aqueous solution of the target compound methanedisulfonic acid.

After the above reactions were completed, the obtained aqueous solution of methanedisulfonic acid was sampling analyzed, and determined that the concentration of methanedisulfonic acid was 51.2% and the total yield was 85.2%.

Example VI

Firstly, a sulphination was performed. To a 500 ml autoclave, were added 200 ml of water, 100 ml of acetonitrile, 50 g of calcium sulfite, 0.5 g of polyethylene glycol-400 and 18 g of dichloromethane, heated up to 180° C. under stirring, and reacted for 10 hours. After the reaction was completed, the solution was cooled to room temperature, and the blow valve was opened to discharge the unreacted dichloromethane, so as to obtain 340 g of the reaction solution containing calcium methanedisulfonate.

Secondly, an acidification was performed. 20 g of a concentrated sulfuric acid with a mass percentage of 98% was dissolved into 180 g of water to prepare a dilute sulfuric acid solution with a mass percentage of 10%. 340 g of the reaction solution obtained after the sulphination was added into a 1,000 ml four-neck reaction flask with a stirrer and a reflux condenser, heated up to 80±2° C. under stirring, and dropwise added with the prepared dilute sulfuric acid solution within 0.5 hour, then kept warm at 80±2° C. for 2 hours to complete the reaction.

Finally, purification was performed. The product after the acidification was cooled to about 10° C., then subjected to pumping filtration by a sand core funnel. The filtrate was collected, and the filter cake was washed with a small amount of deionized water, then the filtrate and the washing liquor were combined. The above combined solution was vacuum concentrated by a rotatory evaporator (the vacuum degree was about 25 mmHg, the oil bath had a temperature of 70~100° C.) to distill 200 g of water. The concentrated solution was placed into 100 ml three-neck reaction flask, heated up to 70° C. under stirring, and decolorized by adding 0.1 g of activated carbon therein and keeping warm for 1 hour. The activated carbon was removed by pumping filtration with the sand core funnel while the solution was hot. The filtrate was collected and placed into a freezer at −10° C. for 24 hours, thus crystallized substances were precipitated, and removed by pumping filtration with the sand core funnel. The resulted 65 g of the solution after removing the crystallized substances was the aqueous solution of the target compound methanedisulfonic acid.

After the above reactions were completed, the obtained aqueous solution of methanedisulfonic acid was sampling analyzed, and determined that the concentration of methanedisulfonic acid was 48.2% and the total yield of the reactions was 84.4%.

What is claimed is:

1. A method for preparing methanedisulfonic acid, comprising an acidification,
    wherein the acidification comprises subjecting a methanedisulfonate to reacting with an acidifier to form a precipitate of a salt of the acidifier and obtain a mixture containing methanedisulfonic acid,
    wherein the methanedisulfonate is one or a mixture of two or more selected from a group consisting of calcium methanedisulfonate, barium methanedisulfonate, ferrous methanedisulfonate, ferric methanedisulfonate, silver methanedisulfonate and lead methanedisulfonate, and
    wherein the acidifier is one or a mixture of two or more selected from a group consisting of sulfuric acid, phosphoric acid, methane sulfonic acid and hydrochloric acid.

2. The method for preparing methanedisulfonic acid according to claim 1, further comprising a sulphination before the acidification,
    wherein the sulphination comprises subjecting a sulphinating reagent to reacting with a dihalomethane to obtain a mixture containing methanedisulfonate; and
    optionally, the method further comprising a purification after the acidification.

3. The method for preparing methanedisulfonic acid according to claim 1, further comprising a purification after the acidification.

4. The method for preparing methanedisulfonic acid according to claim 3, wherein the purification comprises filtering the mixture containing methanedisulfonic acid obtained after the acidification, concentrating the filtrate obtained after the filtration, decolorizing the obtained concentrated filtrate with activated carbon, subjecting the concentrated filtrate to freezing crystallization after removing the activated carbon by filtration, and removing the crystallized substances by filtration, thus obtaining an aqueous solution of methanedisulfonic acid.

5. The method for preparing methanedisulfonic acid according to claim 1, wherein the methanedisulfonate is calcium methanedisulfonate or barium methanedisulfonate.

6. The method for preparing methanedisulfonic acid according to claim 1, wherein the acidification is performed in water or a polar organic solvent, or a mixture thereof.

7. The method for preparing methanedisulfonic acid according to claim 1, wherein a molar ratio of the methanedisulfonate to the acidifier is 1:0.5-4.0.

8. The method for preparing methanedisulfonic acid according to claim 1, wherein a reaction temperature of the acidification is 0–200° C.

9. The method for preparing methanedisulfonic acid according to claim 1, wherein a reaction time of the acidification is 1-24 hours.

10. The method for preparing methanedisulfonic acid according to claim 2, wherein the sulphinating reagent is one or a mixture of two or more selected from a group consisting of calcium thiosulfate, barium thiosulfate, ferrous thiosulfate, calcium bisulfite, barium bisulfite, ferrous bisulfite, calcium sulfite, barium sulfite and ferrous sulfite.

11. The method for preparing methanedisulfonic acid according to claim 2, wherein the dihalomethane is dichloromethane or dibromomethane, or a mixture thereof.

12. The method for preparing methanedisulfonic acid according to claim 2, wherein the catalyst of the sulphination is one or a mixture of two or more selected from a group consisting of sodium dodecyl sulfate, cetyl trimethyl ammonium bromide, dodecyl trimethyl ammonium bromide, polyoxyethylene nonyl phenyl ether, polyethylene glycol-400, polyethylene glycol-600, polyethylene glycol-800, tetraethylammonium chloride, tetraethylammonium bromide, tetrabutylammonium chloride and tetrabutylammonium bromide; and a molar ratio of the catalyst to the dihalomethane is 1:1-2000.

13. The method for preparing methanedisulfonic acid according to claim 2, wherein the sulphination is performed in water or a polar organic solvent, or a mixture thereof.

14. The method for preparing methanedisulfonic acid according to claim 13, wherein the polar organic solvent is one or a mixture of two or more selected from a group consisting of dimethylsulfoxide, hexamethylphosphoric triamide, N,N-dimethylformamide, N,N-dimethylacetamide, acetonitrile, methanol and ethanol.

15. The method for preparing methanedisulfonic acid according to claim 2, wherein a molar ratio of the sulphinating reagent to the dihalomethane is 1:0.1-10.

16. The method for preparing methanedisulfonic acid according to claim 2, wherein a reaction temperature of the sulphination is 40–220° C.

17. The method for preparing methanedisulfonic acid according to claim 2, wherein a reaction time of the sulphination is 1-24 hours.

18. The method for preparing methanedisulfonic acid according to claim 2, wherein the purification comprises filtering the mixture containing methanedisulfonic acid obtained after the acidification, concentrating the filtrate obtained after the filtration, decolorizing the obtained concentrated filtrate with activated carbon, subjecting the concentrated filtrate to freezing crystallization after removing the activated carbon by filtration, and removing the crystallized substances by filtration, thus obtaining an aqueous solution of methanedisulfonic acid.

19. The method for preparing methanedisulfonic acid according to claim 6, wherein the polar organic solvent is one or a mixture of two or more selected from a group consisting of dimethylsulfoxide, hexamethylphosphoric triamide, N,N-dimethylformamide, N,N-dimethylacetamide, acetonitrile, methanol and ethanol.

* * * * *